United States Patent
Giovannini et al.

(10) Patent No.: US 6,394,946 B1
(45) Date of Patent: May 28, 2002

(54) TREATMENT OF CELLULITE

(75) Inventors: Paolo Giovannini, Aosta (IT); Roger Jubert, Cannes (FR); Edmondo Giovannini, Brussels (BE)

(73) Assignee: Mir Magnetic Institute Research S.A., Lugano Paradiso (CH)

( * ) Notice: Subject to any disclaimer, the term of this patent is extended or adjusted under 35 U.S.C. 154(b) by 0 days.

(21) Appl. No.: 09/579,269

(22) Filed: May 26, 2000

(51) Int. Cl.7 .................................................. A61N 1/00
(52) U.S. Cl. ......................................................... 600/15
(58) Field of Search ............................... 600/15, 9, 13, 600/14; 252/62.54; 2/159, 160

(56) References Cited

U.S. PATENT DOCUMENTS

| | | | |
|---|---|---|---|
| 3,764,539 A | * 10/1973 | Cochardt et al. | ........ 252/62.54 |
| 5,720,046 A | * 2/1998 | Lopez et al. | ................... 600/15 |
| 6,006,363 A | * 12/1999 | Karlin | ........................ 600/15 |

* cited by examiner

Primary Examiner—Kevin Shaver
Assistant Examiner—Brian Szmal
(74) Attorney, Agent, or Firm—Sughrue Mion, PLLC

(57) ABSTRACT

The shorts comprise a plurality of essentially two-dimensional, permanently magnetized, flexible elements. Each principal face of said elements has a magnetic polarity opposed to that of the other face. Said elements are applied to prearranged portions of the shorts in such a manner that, in use, they impart the same magnetic polarity to the body of the user.

6 Claims, 3 Drawing Sheets

TREATMENT OF CELLULITE

BACKGROUND OF THE INVENTION

The present invention relates in general to the treatment of cellulite.

Cellulite is a manifestation arising from processes of varying nature, such as inflammatory processes and the processes of infiltration of liquids and toxins into the subcutaneous adipose tissue.

The body areas more typically affected by such manifestations are the hips and legs, in particular the inside and the back of the thighs.

From experiments carried out it has emerged that the exposure of the areas affected by cellulite to a relatively weak magnetic field may have beneficial effects in the reduction of the imperfections caused by the cellulite.

SUMMARY OF THE INVENTION

The aim of the present invention is to make it possible to carry out in an easy, comfortable and relatively economic manner a topical treatment for cellulite by means of the localized application of a magnetic field to the body areas more typically affected by this phenomenon.

BRIEF DESCRIPTION OF THE DRAWINGS

Further characteristics and advantages of the invention will become clear from the following detailed description, provided solely by way of non-limiting example, with reference to the appended drawings, in which.

DETAILED DESCRIPTION OF THE INVENTION

Figure 1:
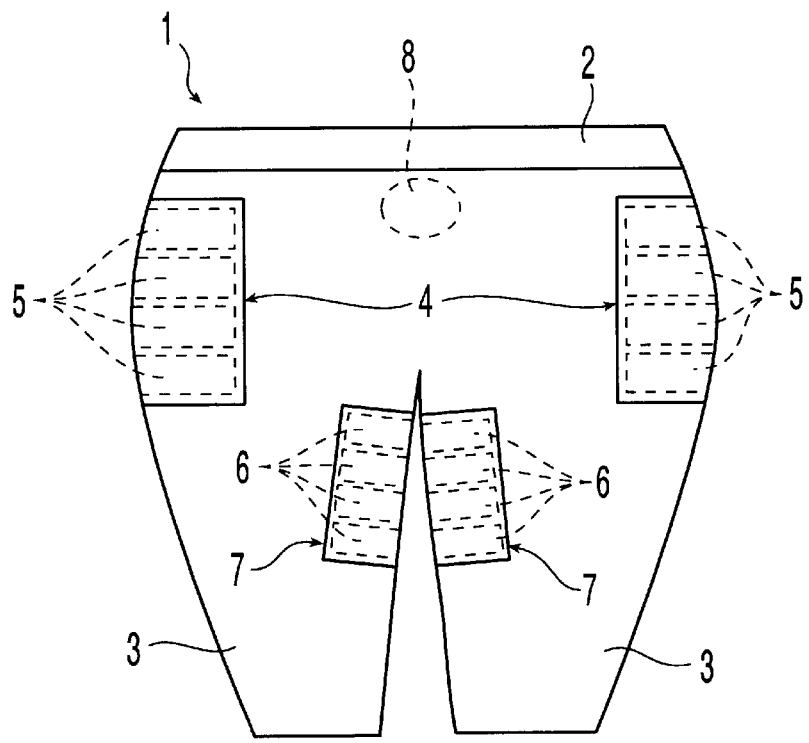
FIG. 1 is a front view of a pair of shorts according to the invention.

In FIG. 1, the reference 1 indicates as a whole a pair of shorts for the topical treatment of cellulite according to the invention.

The shorts are preferably produced from an elastic fabric, composed for example of 90% cotton and 10% synthetic elastic yarn, for example of the type marketed under the brand name "Lycra".

In the exemplary embodiment illustrated, the shorts 1 are provided with an elastic strip 2 in the region of the waist, having, for example, a height of about 35 mm.

The shorts 1 have two tubular portions or legs 3, preferably having a length such as to cover the thighs of the user substantially as far as the knee.

To each portion of the shorts 1 corresponding to a user's hip there are applied, preferably on the outside, respective rectangular pieces 4. Said pieces are applied preferably by means of flat stitching with double needle.

Figure 5:
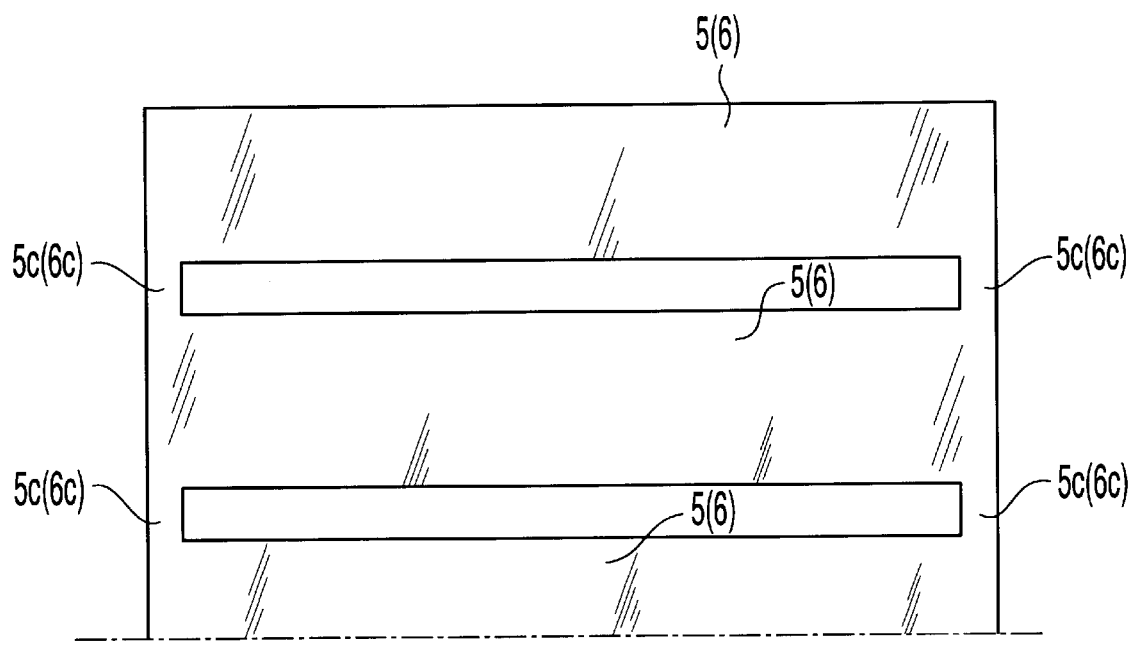
FIG. 5 is a partial plan view of a group of permanently magnetized flexible elements used for the production of a pair of shorts according to the invention.

Between each piece 4 and the corresponding portion of the shorts 1 there is interposed a respective plurality of essentially two-dimensional, permanently magnetized, flexible elements 5. One of said flexible elements is shown in FIG. 5.

The flexible magnetized elements 5 consist for example of an elastomeric material charged with a ferrite powder.

Figure 3:
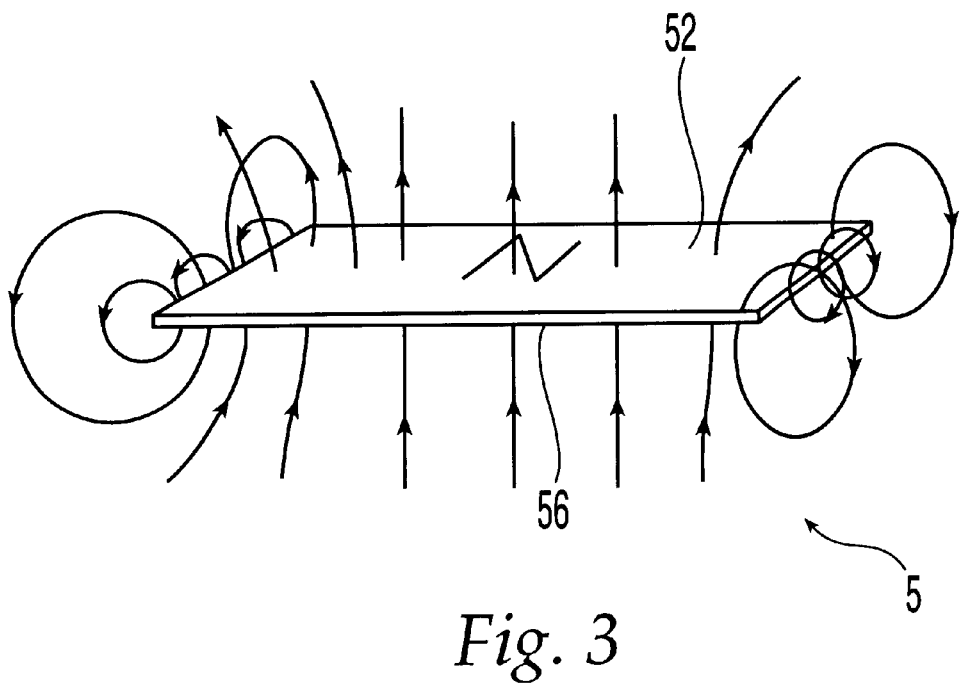
FIG. 3 is a perspective view which shows a permanently magnetized flexible element used in the shorts according to the invention.
Figure 4:
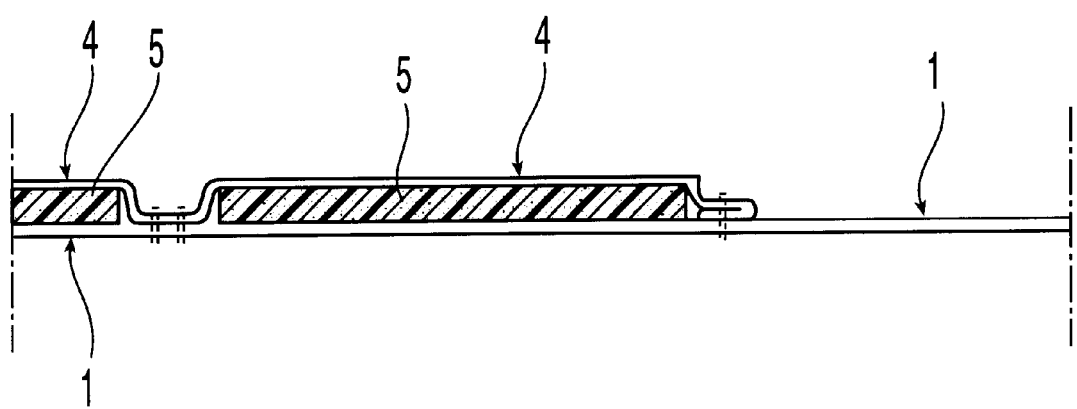
FIG. 4 is a partial view in section along the line IV—IV in FIG. 2.

Each flexible magnetized element 5 is produced in such a manner that each of the two principal faces has a magnetic polarity opposed to that of the other face. In other words if, referring to FIG. 3, a principal face 5a of such an element has a magnetic polarity of the "North" type, the opposed principal face 5b has a polarity of the "South" type. Consequently, as shown qualitatively in FIG. 3, each magnetized element 5 generates a magnetic field, the lines of flux of which are essentially parallel to one another, except in proximity to the margins of the element.

Each flexible magnetized element is produced preferably in such a manner that it is capable of generating a magnetic flux having an intensity of between approximately 300 and 400 Gauss.

The flexible magnetized elements 5 arranged on the hips of the shorts 1 have an elongate form, in particular a rectangular form, and are arranged so as to be substantially parallel to one another and to the waistline of the shorts.

In the embodiment according to FIG. 1, a further plurality of flexible magnetized elements 6 is applied to a respective inner portion of each leg 3 of the shorts. Said elements 6 may conveniently be identical to the elements 5 mentioned previously.

The flexible magnetized elements 6 are also conveniently interposed between the surface of the shorts 1 and respective retaining pieces 7 stitched (preferably on the outside) to the shorts.

Preferably, in order to facilitate the production of the shorts, each group of flexible magnetized elements 5 or 6 is produced as a one piece assembly, in which the individual elements 5 or 6 are interconnected by small bridges integral therewith, as shown in FIG. 5. In the said figure the interconnecting bridges between the various flexible magnetized elements of each plurality are indicated by 5c (6c). Owing to said bridges, the individual groups of flexible magnetized elements 5 or 6 can be easily manipulated and readily applied to the shorts in the uniformly spaced arrangement provided for.

The application of the flexible magnetized elements 5 or 6 and of the associated retaining pieces 4 and 7 is conveniently effected by means of stitching, preferably carried out along the perimeter of said pieces and also in the interstices between the adjacent flexible magnetized elements.

In each case, the flexible magnetized elements should be applied to the shorts in such a manner that, in use, they impart the same magnetic polarity to the body of the user.

The solution described above with reference to FIG. 5 also has the advantage of guaranteeing that all the flexible magnetized elements of each group are correctly applied, from the magnetic point of view, to the shorts.

Figure 6:
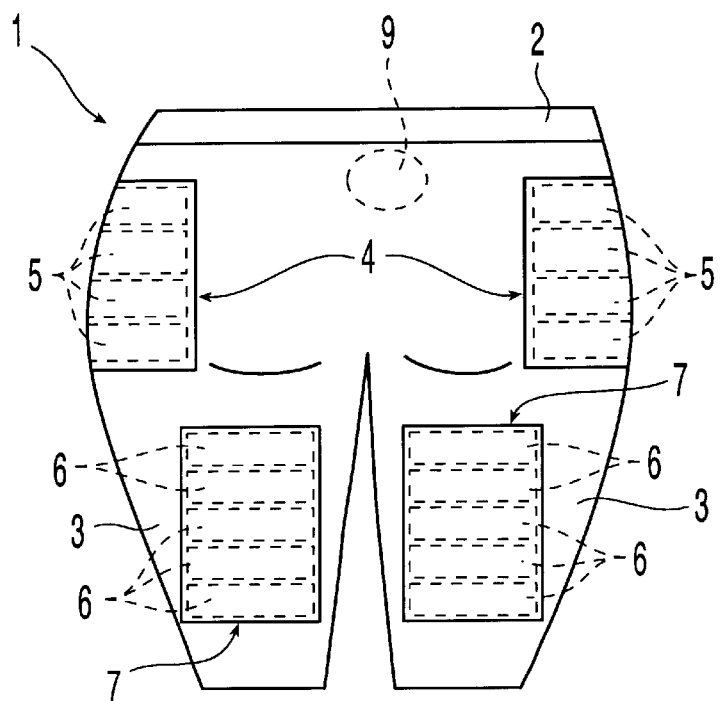
FIG. 6 is a rear view of another pair of shorts according to the invention.

FIG. 6 shows a variant embodiment. In said figure, the same reference numbers have been assigned again to parts and elements already described.

Figure 2:
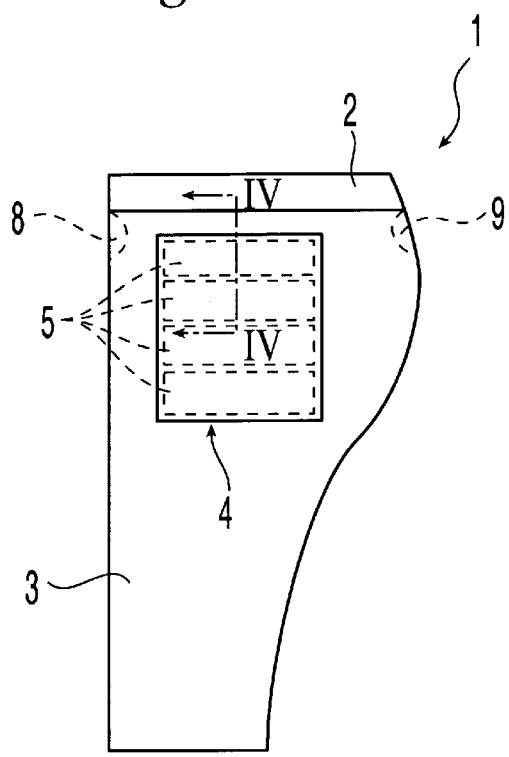
FIG. 2 is a side view of the shorts according to FIG. 1.

In said variant, the flexible magnetized elements 6 are applied to a rear portion of each leg 3 of the shorts, and therefore at the rear part of the user's thighs. Said parts are in fact other typical sites affected by the formation of cellulite. Preferably, a pair of shorts according to the invention is further provided with a further flexible, permanently magnetized element, applied to a front portion of the shorts corresponding essentially to the umbilical area of the user. In FIGS. 1 and 2, said flexible magnetized element is indicated by 8. A further flexible magnetized element is conveniently also applied to a rear portion of the shorts 1, corresponding substantially to the sacral area of the user, as can be seen in FIGS. 2 and 6, in which said further magnetized element is indicated by 9.

The magnetized elements 8 and 9 conveniently have a circular shape and can be applied to the shorts on the inside or the outside, using complementary retaining pieces stitched to the shorts themselves.

The flexible magnetized elements 5 or 6 may have, as an indication, a length of about 15 cm, a width of 2.5 cm and a thickness of between 1 and 2 mm.

The flexible magnetized elements 8 and 9 may have a diameter of about 5 cm, and a thickness, in this case also, which is preferably between 1 and 2 mm.

The shorts according to the invention are extremely comfortable and practical in use. They may be worn while carrying out any activity.

From tests carried out, it has proved that good results are obtained by wearing the shorts on average for (a total of) 2–3 hours in the space of one day.

Naturally, while the principle of the invention remains the same, the forms of implementation and the details of production may be widely varied with respect to what has been described and illustrated solely by way of non-limiting example, without thereby departing from the scope of the invention as defined in the appended claims.

What is claimed is:

1. Shorts for the topical treatment of cellulite comprised of a substanitally elastic fabric and having a body portion, a waistband and a pair of leg portions, a plurality of elongated substantially rectangular magnetized flexible elements with each principle face of each element having a magnetic polarity opposed to that of an opposite face, said elements being secured to the shorts in such a manner that in use they impart the same magnetic polarity to the body of the user, wherein a first plurality of said elements is secured to each portion of the shorts corresponding to a user's hip and a second plurality of said elements is secured to an inner portion of each leg portion of the shorts, said elements in each plurality of elements being parallel to each other and to the waistband of said shorts and wherein each of said elements is comprised of an elastimeric material charged with a ferrite powder capable of generating a magnetic flux having an intensity of between approximately 300 and approximately 400 Gauss.

2. Shorts according to claim 1, wherein a plurality of said elements is applied to a rear portion of each leg portion of the shorts.

3. Shorts according to claim 1 further comprising at least one flexible permanently magnetized element having a substantially circular shape applied to a front portion of the shorts corresponding substantially to the umbilical area of the user.

4. Shorts according to claim 1 wherein at least one flexible permanently magnetized element having a substantially circular shape is applied to a rear portion of the shorts corresponding substantially to the sacral area of the user.

5. Shorts according to claim 1 wherein said elements of each plurality of elements are interposed between a portion of the shorts and a retaining pieces, the edges of which are secured to the shorts.

6. Shorts according to claim 1 wherein the elements of each plurality of elements is are each connected by small bridges integral therewith.

* * * * *